United States Patent
Sanson Giraldo et al.

(10) Patent No.: US 11,206,983 B2
(45) Date of Patent: Dec. 28, 2021

(54) BRAIN IMAGE DATA PROCESSING APPARATUS, BRAIN IMAGE DATA PROCESSING METHOD, AND BRAIN IMAGE DATA PROCESSING PROGRAM

(71) Applicant: Allm Inc., Tokyo (JP)

(72) Inventors: Horacio Sanson Giraldo, Tokyo (JP); Fernando Javier Wong Kwai Ben, Tokyo (JP); Tadashi Masuoka, Kanagawa (JP); Hiroyuki Takao, Tokyo (JP)

(73) Assignee: Allm Inc., Tokyo (JP)

( * ) Notice: Subject to any disclaimer, the term of this patent is extended or adjusted under 35 U.S.C. 154(b) by 228 days.

(21) Appl. No.: 16/616,422

(22) PCT Filed: May 11, 2018

(86) PCT No.: PCT/JP2018/018280
§ 371 (c)(1),
(2) Date: Nov. 22, 2019

(87) PCT Pub. No.: WO2018/216504
PCT Pub. Date: Nov. 29, 2018

(65) Prior Publication Data
US 2020/0178804 A1 Jun. 11, 2020

(30) Foreign Application Priority Data
May 26, 2017 (JP) .............................. JP2017-104337

(51) Int. Cl.
*G06K 9/00* (2006.01)
*A61B 6/00* (2006.01)
(Continued)

(52) U.S. Cl.
CPC .......... *A61B 5/0042* (2013.01); *A61B 5/4064* (2013.01); *G06T 7/0012* (2013.01);
(Continued)

(58) Field of Classification Search
USPC ....... 382/100, 103, 106, 128–132, 154, 168, 382/172–173, 181, 199, 209, 224, 254,
(Continued)

(56) References Cited

U.S. PATENT DOCUMENTS 6,788,816 B1 * 9/2004 Kiyuna ................ G06T 7/0012
382/199
10,262,414 B2 * 4/2019 Nitzken ................ G06T 7/0012
(Continued)

FOREIGN PATENT DOCUMENTS

JP 2001-092980 A 4/2001
JP 2007-289704 A 11/2007
(Continued)

OTHER PUBLICATIONS

International Search Report (ISR) dated Jul. 10, 2018 filed in PCT/JP2018/018280.

*Primary Examiner* — Seyed H Azarian
(74) *Attorney, Agent, or Firm* — Rankin, Hill & Clark LLP

(57) ABSTRACT

An object of the present disclosure is to improve setting accuracy of site regions in brain image data. A brain image data processing apparatus 100 includes: a brain image data reading unit for reading brain image data in which the site regions for identifying each site are set at positions corresponding to each site of a brain; a probability calculation unit for calculating a probability that each pixel is included in each site region based on a distance between each pixel and each site region for each pixel not included in any site region in the brain image data read by the brain image data reading unit; and a determination unit for determining which site region each pixel belongs to, based on the probability calculated by the probability calculation unit.

15 Claims, 7 Drawing Sheets

(51) Int. Cl.
*A61B 5/00* (2006.01)
*G06T 7/143* (2017.01)
*G06T 7/11* (2017.01)
*G06T 7/00* (2017.01)

(52) U.S. Cl.
CPC ............... *G06T 7/11* (2017.01); *G06T 7/143* (2017.01); *G06T 2207/20076* (2013.01); *G06T 2207/30016* (2013.01)

(58) Field of Classification Search
USPC ..... 382/285–291, 305, 318; 324/309; 378/4, 378/21
See application file for complete search history.

(56) References Cited

U.S. PATENT DOCUMENTS

| | | | |
|---|---|---|---|
| 2007/0019846 A1* | 1/2007 | Bullitt | G06T 7/0014 382/128 |
| 2008/0033302 A1 | 2/2008 | Grady et al. | |
| 2008/0298653 A1 | 12/2008 | Amunts et al. | |
| 2009/0226060 A1 | 9/2009 | Gering et al. | |
| 2010/0322496 A1 | 12/2010 | Liu et al. | |
| 2011/0033099 A1 | 2/2011 | Kadomura et al. | |
| 2015/0309142 A1* | 10/2015 | Li | G01R 33/5611 324/309 |
| 2017/0018089 A1* | 1/2017 | Garnavi | G06T 7/10 |

FOREIGN PATENT DOCUMENTS

| | | |
|---|---|---|
| JP | 2009-518060 A | 5/2009 |
| JP | 2011-512999 A | 4/2011 |
| JP | 2011-514190 A | 5/2011 |
| WO | 2009/131109 A1 | 10/2009 |

\* cited by examiner

BRAIN IMAGE DATA PROCESSING APPARATUS, BRAIN IMAGE DATA PROCESSING METHOD, AND BRAIN IMAGE DATA PROCESSING PROGRAM

TECHNICAL FIELD

The present invention relates to a brain image data processing apparatus, a brain image data processing method, and a brain image data processing program.

BACKGROUND ART

The following contour extraction apparatus is known. In the contour extraction apparatus, with respect to the image data including an image of an object to be subjected to contour extraction, points of the image are separated into a plurality of regions to which the points belong based on an attribute possessed by each of the points, and a boundary between the regions is extracted as a contour, so that an MRI image of human head is classified into three regions of brain, scalp, and other than head (see Patent Literature 1).

CITATION LIST

Patent Literature

Patent Literature 1: JP-A-2001-092980

SUMMARY OF THE INVENTION

Problems to be Solved by the Invention

There is a technique for analyzing the MRI image and dividing the image into a plurality of regions as in the conventional contour extraction apparatus. When the image is divided into the plurality of regions as described above, division of the regions may not be correctly performed depending on processing accuracy. For example, when performing region division on each site in the brain in a brain image, there is a possibility that pixels that should be originally included in the region corresponding to any site are divided so as not to belong to any image region. In the related art, no study has been made on a technique for determining in which region each pixel should be included in such a case.

Solution to the Problems

According to a first aspect of the present invention, a brain image data processing apparatus includes: a brain image data reading unit for reading brain image data in which site regions for identifying each site are set at positions corresponding to each site of a brain; a probability calculation unit for calculating a probability that each pixel is included in each site region based on a distance between each pixel and each site region for each pixel not included in any site region in the brain image data read by the brain image data reading unit; and a determination unit for determining which site region each pixel belongs to, based on the probability calculated by the probability calculation unit.

According to a second aspect of the present invention, in the brain image data processing apparatus of the first aspect, the probability calculation unit calculates a geodesic distance between each pixel and each site region for each pixel not included in any site region, and calculates the probability that each pixel is included in each site region based on the geodesic distance.

According to a third aspect of the present invention, in the brain image data processing apparatus of the first or the second aspect, the determination unit determines that a target pixel belongs to the site region when the probability calculated by the probability calculation unit is larger than a preset threshold value.

According to a fourth aspect of the present invention, the brain image data processing apparatus of any one of the first to the third aspects further includes an updating unit for updating the setting of the site region in the brain image data so as to include the pixel determined to belong to each site region based on a determination result by the determination unit.

According to a fifth aspect of the present invention, the brain image data processing apparatus of the fourth aspect further includes a process repeating unit for repeating a process by the probability calculation unit, the determination unit, and the updating unit until a preset stop condition is satisfied, for the brain image data in which the setting of the site region has been updated by the updating unit.

According to a sixth aspect of the present invention, in the brain image data processing apparatus of the fifth aspect, the process repeating unit determines that the stop condition is satisfied when the setting of the site region in the brain image data has not changed from a previous process.

According to a seventh aspect of the present invention, in the brain image data processing apparatus of the fifth aspect, the process repeating unit determines that the stop condition is satisfied when the number of repetitions of the process reaches a preset number.

According to an eighth aspect of the present invention, a brain image data processing method is a method for causing a computer to perform the following steps: a brain image data reading step of reading brain image data in which site regions for identifying each site are set at positions corresponding to each site of a brain; a probability calculation step of calculating a probability that each pixel is included in each site region based on a distance between each pixel and each site region for each pixel not included in any site region in the brain image data read in the brain image data reading step; and a determination step of determining which site region each pixel belongs to, based on the probability calculated by the probability calculation step.

According to a ninth aspect of the present invention, in the brain image data processing method of the eighth aspect, the probability calculation step calculates a geodesic distance between each pixel and each site region for each pixel not included in any site region, and calculates the probability that each pixel is included in each site region based on the geodesic distance.

According to a tenth aspect of the present invention, in the brain image data processing method of the eighth or the ninth aspect, the determination step determines that a target pixel belongs to the site region when the probability calculated by the probability calculation step is larger than a preset threshold value.

According to an eleventh aspect of the present invention, the brain image data processing method of any one of the eighth to the tenth aspects further includes an updating step for updating setting of the site region in the brain image data so as to include the pixel determined to belong to each site region based on a determination result by the determination step.

According to a twelfth aspect of the present invention, the brain image data processing method of the eleventh aspect further includes a process repeating step of repeating a process by the probability calculation step, the determination step, and the updating step until a preset stop condition is satisfied, for the brain image data in which the setting of the site region has been updated by the updating step.

According to a thirteenth aspect of the present invention, in the brain image data processing method of the twelfth aspect, the process repeating step determines that the stop condition is satisfied when the setting of the site region in the brain image data has not changed from a previous process.

According to a fourteenth aspect of the present invention, in the brain image data processing method of the twelfth aspect, the process repeating step determines that the stop condition is satisfied when the number of repetitions of the process reaches a preset number.

According to a fifteenth aspect of the present invention, a brain image data processing program is a program for causing a computer to perform the following steps: a brain image data reading step of reading brain image data in which site regions for identifying each site are set at positions corresponding to each site of a brain; a probability calculation step of calculating a probability that each pixel is included in each site region based on a distance between each pixel and each site region for each pixel not included in any site region in the brain image data read in the brain image data reading step; and a determination step of determining which site region each pixel belongs to, based on the probability calculated by the probability calculation step.

According to a sixteenth aspect of the present invention, in the brain image data processing program of the fifteenth aspect, the probability calculation step calculates a geodesic distance between each pixel and each site region for each pixel not included in any site region, and calculates the probability that each pixel is included in each site region based on the geodesic distance.

According to a seventeenth aspect of the present invention, in the brain image data processing program of the fifteenth or the sixteenth aspect, the determination step determines that a target pixel belongs to the site region when the probability calculated by the probability calculation step is larger than a preset threshold value.

According to an eighteenth aspect of the present invention, the brain image data processing program of any one of the fifteenth to the seventeenth aspects further includes an updating step for updating the setting of the site region in the brain image data so as to include the pixel determined to belong to each site region based on a determination result by the determination step.

According to a nineteenth aspect of the present invention, the brain image data processing program of the eighteenth aspect further includes a process repeating step of repeating a process by the probability calculation step, the determination step, and the updating step until a preset stop condition is satisfied, for the brain image data in which the setting of the site region has been updated by the updating step.

According to a twentieth aspect of the present invention, in the brain image data processing program of the nineteenth aspect, the process repeating step determines that the stop condition is satisfied when the setting of the site region in the brain image data has not changed from a previous process.

According to a twenty-first aspect of the present invention, in the brain image data processing program of the nineteenth aspect, the process repeating step determines that the stop condition is satisfied when the number of repetitions of the process reaches a preset number.

Effect of the Invention

According to the present invention, it is possible to determine which site region should each pixel not yet included in any site region belongs to, for the brain image data in which the site regions are set.

DESCRIPTION OF THE EMBODIMENTS

Figure 1:
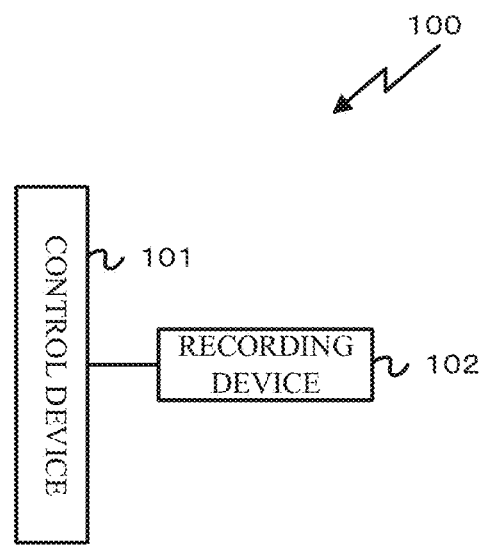
FIG. 1 is a block diagram showing a configuration of an embodiment of a brain image data processing apparatus 100.

FIG. 1 is a block diagram showing a configuration of an embodiment of a brain image data processing apparatus 100 according to the present embodiment. For example, a server apparatus, a personal computer or the like is used as the brain image data processing apparatus 100, and FIG. 1 shows the configuration of the embodiment in the case where the server apparatus is used as the brain image data processing apparatus 100. The brain image data processing apparatus 100 includes a control device 101 and a recording device 102.

The control device 101 includes a CPU, a memory, and other peripheral circuits, and controls the entire brain image data processing apparatus 100. The memory constituting the control device 101 is, for example, a volatile memory such as an SDRAM. The memory is used as a work memory for the CPU to develop a program when executing the program, and a buffer memory for temporarily recording the data.

The recording device 102 is a recording device for recording various data stored by the brain image data processing apparatus 100, the data of the program to be executed by the control device 101, and the like. As the recording device 102, for example, a hard disk drive (HDD), a solid state drive (SSD) or the like is used. The data of the program recorded in the recording device 102 is provided by being recorded in a recording medium such as a CD-ROM or a DVD-ROM, or provided via a network, and an operator installs the obtained data of the program in the recording device 102, so that the control device 101 can execute the program.

In the brain image data processing apparatus 100 according to the present embodiment, brain image data obtained by imaging a brain of a subject is recorded in the recording device 102 in advance. The brain image data of the subject taken by MRI, CT or the like is used as the brain image data.

Further, in the present embodiment, in the brain image data of the subject, site regions for identifying each site are set at positions corresponding to each site of the brain. Since a method of setting the site region is performed in advance using a known method, and is not limited, a detailed description thereof will be omitted here. An example of the method of setting the site region includes dividing the brain image data into the regions based on a density value of each pixel in the image using a threshold value set in advance, or preparing a template image imitating a shape of each site of the brain to divide the brain image data into the regions for each site of the brain by shape matching process using the template image.

Figure 2:
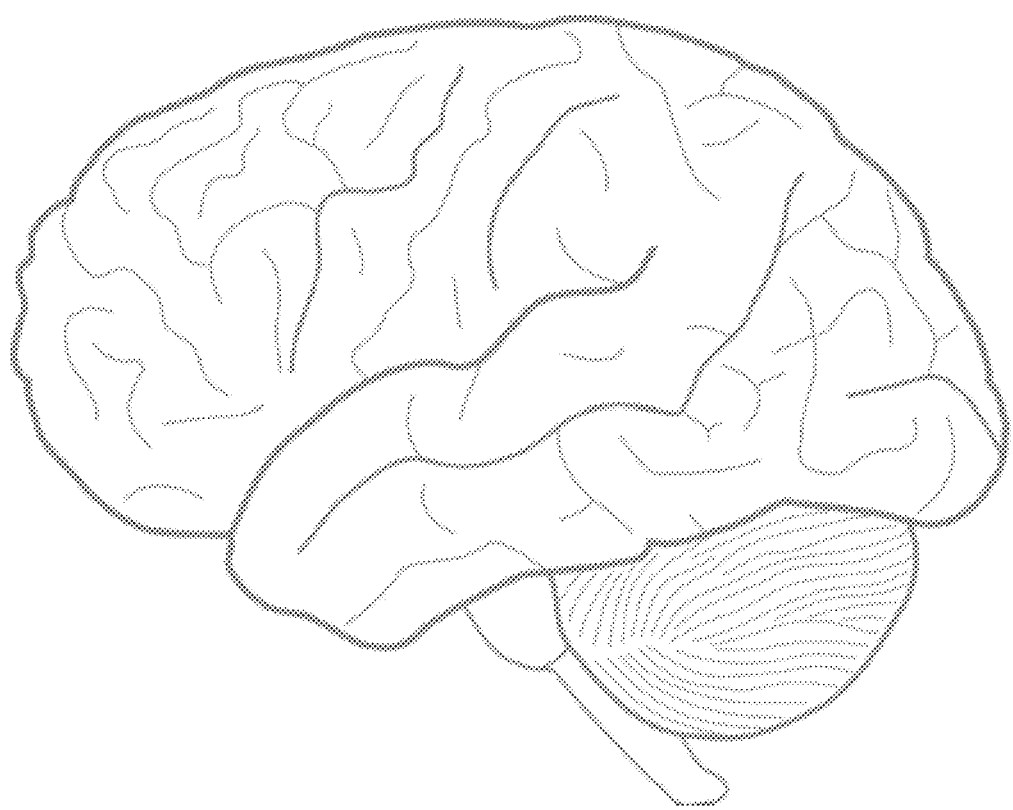
FIG. 2 is a view schematically showing an example of brain image data.
Figure 3:
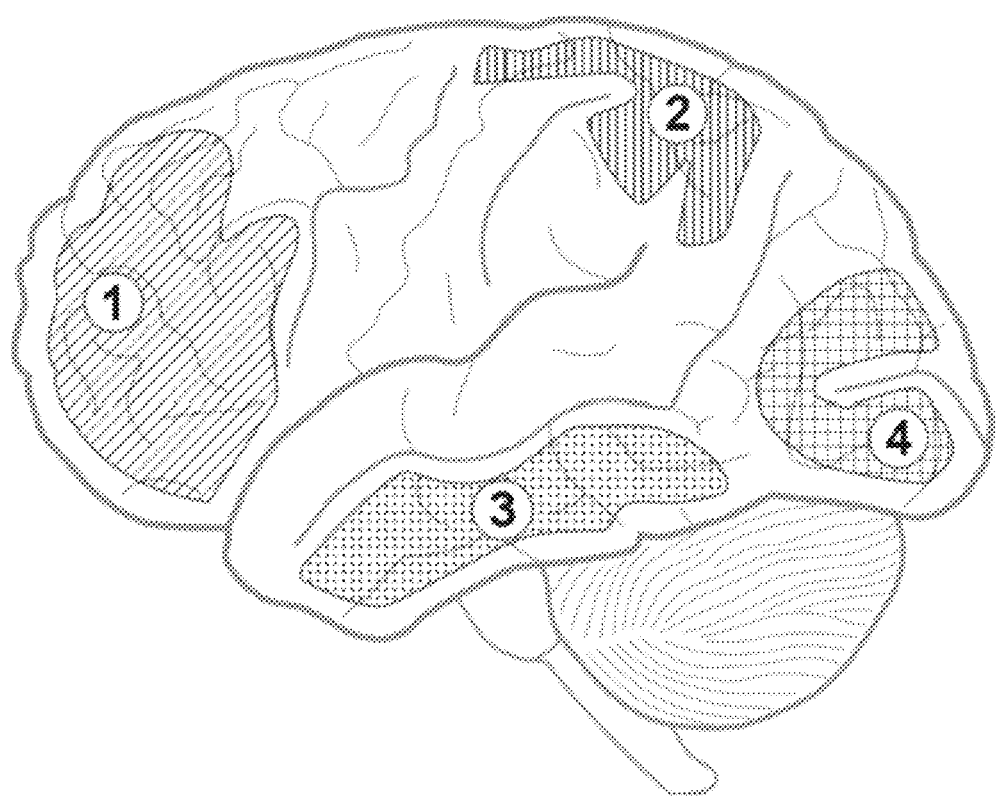
FIG. 3 is a view schematically showing an example of setting a site region in the brain image data.

For example, with respect to the brain image data as shown in FIG. 2, a site region 1, a site region 2, a site region 3, and a site region 4 are set at positions corresponding to each site of the brain as shown in FIG. 3. In FIG. 3, the site region 1 indicates a region set for a frontal lobe, the site region 2 indicates a region set for a parietal lobe, the site region 3 indicates a region set for a temporal lobe, and the site region 4 indicates a region set for an occipital lobe.

As described above, division into regions for each site performed in advance in the brain image data is not necessarily accurate. Therefore, there is a possibility that a pixel originally belonging to any site region may be located outside the site region. In the present embodiment, in order to solve such a problem, a method of updating the site region will be described, in which it is determined whether a pixel not included in the site region should belong to an site region, so that the pixel determined to belong to any site region is included in the site region to which the pixel originally belongs.

The control device 101 reads the brain image data set with the site regions from the recording device 102, calculates a probability that each pixel not included in any site region is included in each site region based on a distance between each pixel and each site region, and determines to which site region each pixel belongs, based on the calculated probability. In the present embodiment, it is assumed that L site regions are set for brain image data I including n pixels, and the following process is performed.

The control device 101 initializes a binary map Bi using the following equation (1) for each site region set in the read brain image data.

[Equation 1]

$$B_i(x) = \begin{cases} 1, & \text{if } A(x) = I_i \\ 0, & \text{otherwise} \end{cases} \quad (1)$$

In Equation (1), x indicates the pixel in the brain image data, and A(x) indicates the site region including the pixel x. $I_i$ indicates a label for identifying each site region. In the present embodiment, for example, it is assumed that a label $I_1$ is assigned to the site region 1 shown in FIG. 3, a label $I_2$ is assigned to the site region 2, a label $I_3$ is assigned to the site region 3, and a label $I_4$ is assigned to the site region 4. Therefore, $B_i(x)$ can be obtained by Equation (1), in which the pixels belonging to the site region to which the label $I_1$ is assigned are initialized to a value of 1, and the pixels not belonging to the site region to which the label $I_1$ is assigned are initialized to a value of 0. For example, in $B_1(x)$, the pixels belonging to the site region 1 are initialized to the value of 1, and the pixels not belonging to the site region 1 are initialized to the value of 0, so that the pixels are binarized.

The control device 101 uses the following equation (2) to calculate a geodesic distance D(x, B, I) along the line connecting each pixel x and each site region $I_i$ for each pixel not included in any site region. In the following equation (2), d(x, y) is calculated by the following equation (3). In the following equation (3), $P_{x, y}$ is a set of all paths between the pixel x and a pixel y, and p is one path between the pixel x and the pixel y, and is parametrized by s taking the value of 0 or 1. $\nabla I(s)$ is a gradient of the brain image data I at a position s of a path p, and p'(s) is a direction vector of the path p, and is calculated by the following equation (4). A constant γ is a constant for adjusting contribution of image gradient $\nabla I(s)$ to a total distance from the pixel x to the pixel y along the path p. In a normal distance transformation calculation, γ=0.

[Equation 2]

$$D(x, B, I) = \min_{\{y | B(y) = 1\}} d(x, y) \quad (2)$$

[Equation 3]

$$d(x, y) = \min_{p \in P_{x,y}} \int_0^{|p|} \sqrt{\|p'(s)\|^2 + \gamma^2 (\nabla I(s) \cdot p'(s))^2} ds \quad (3)$$

$$p'(s) = p(s+1) - p(s) \quad (4)$$

The control device 101 can calculate the geodesic distance D(x, B, I) between each site region $I_i$ and each pixel x by performing the above process.

Figure 4:
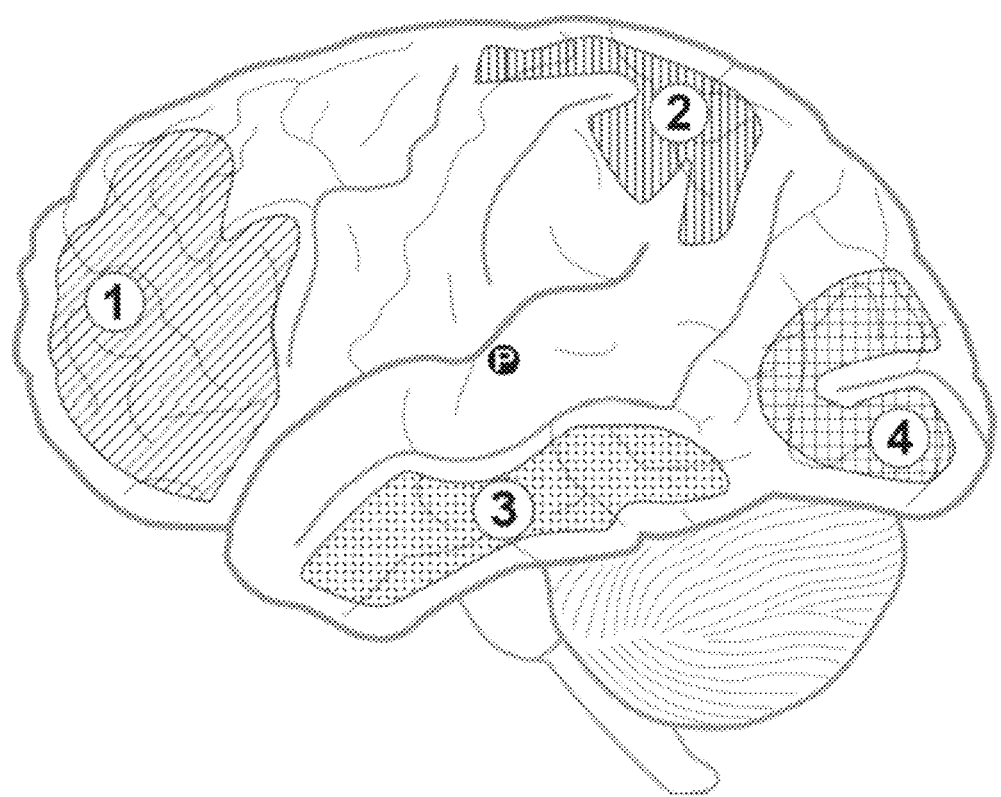
FIG. 4 is a view schematically showing an example of setting a pixel P in the brain image data.
Figure 5:
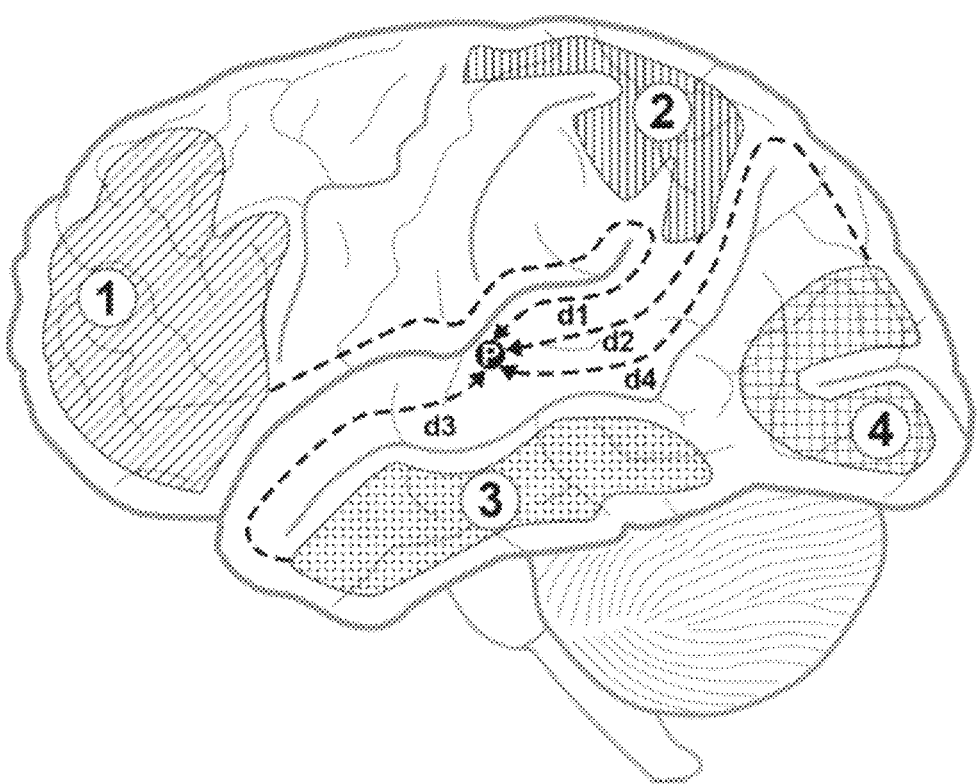
FIG. 5 is a view schematically showing a geodesic distance between each site region and the pixel P in the brain image data.

For example, with respect to the pixel P shown in FIG. 4, as shown by broken lines in FIG. 5, d1 is calculated as the geodesic distance D(x, B, I) between a point P and the site region 1, d2 is calculated as the geodesic distance D(x, B, I) between the point P and the site region 2, d3 is calculated as the geodesic distance D(x, B, I) between the point P and the site region 3, and d4 is calculated as the geodesic distance D(x, B, I) between the point P and the site region 4 by Equation (2).

The control device 101 calculates a probability $p(x|I_i)$ that each pixel x belongs to each site region $I_i$ by the following equation (5) based on the geodesic distance D(x, B, I) calculated by the above process. In the present embodiment, a probability that each pixel x belongs to each of n site regions $I_1, I_2, \ldots, I_n$ is calculated as $p(x) = (p(x|I_1), p(x|I_2), \ldots, p(x|I_n))$ using the following equation (5). In the following equation (5), when L site regions are set in the brain image data I as described above, n=L.

[Equation 4]

$$p(x | I_i) = 1 - \frac{D_i(x, B_i, I)}{\sum_{j \in n} D_j(x, B_j, I)} \quad (5)$$

After calculating the probability for each pixel, the control device 101 determines to which site region the pixel x belongs to by the following equation (6). That is, when the highest calculated probability in p(x) calculated using Equation (5) is larger than a threshold value t set in advance, the control device 101 determines that the pixel x belongs to the site region in which the highest probability has been calculated by Equation (5), and updates information of a site region A(x) including the pixel x. On the other hand, when the highest probability calculated by Equation (5) is smaller than the threshold value t set in advance, the control device 101 determines that the pixel x does not belong to any site region and sets A(x)=0.

[Equation 5]

$$A(x) = \begin{cases} \operatorname{argmax}_{l_i} p(x \mid l_i), & \text{if } \max_{l_i} p(x \mid l_i) > t, \\ 0, & \text{otherwise} \end{cases} \quad (6)$$

Figure 6:
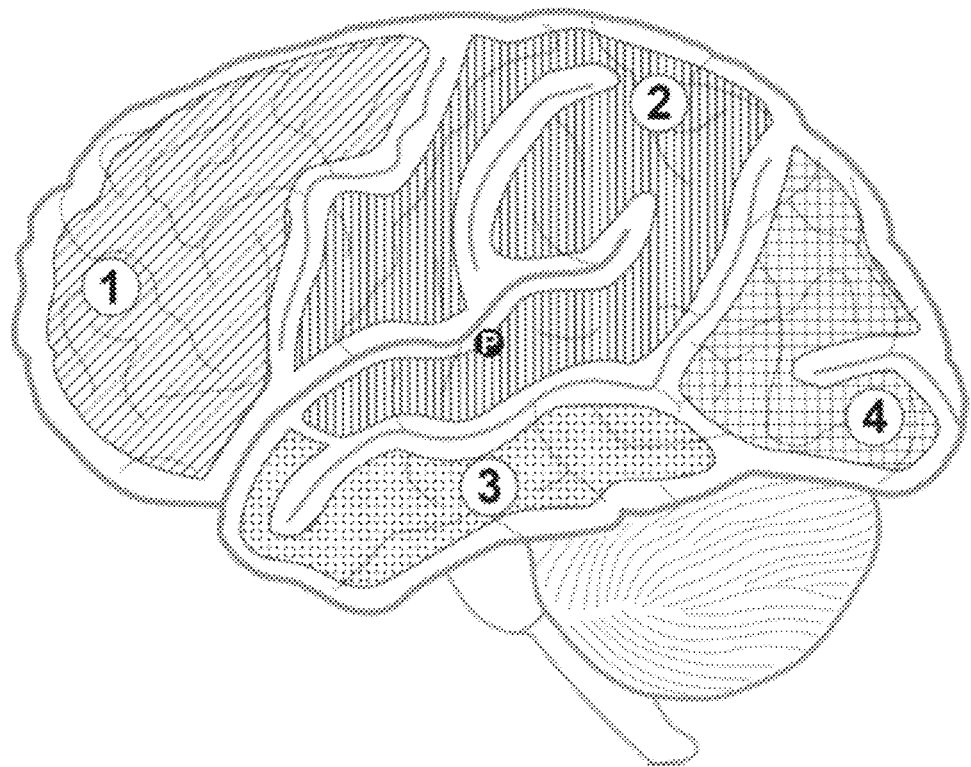
FIG. 6 is a view schematically showing an example of updating the site region in the brain image data.

Thus, the control device 101 can determine the site region corresponding to an original site for the pixels not initially belonging to any site region on the input brain image data I. The control device 101 updates the setting of the site region so that the pixel newly determined to belong to the site region belongs to each site region in the brain image data based on result of Equation (6), to obtain the new brain image data. For example, in FIG. 6, the site region 2 is expanded to include the pixel P, and the other site regions are also expanded and updated to include surrounding pixels.

The control device 101 newly reads the brain image data after updating the setting of the site region and repeats the above process, so that setting accuracy of the site region in the brain image data can be improved. Although the number of times to repeat the process is not particularly limited, for example, when the setting of the site region in the brain image data is not changed from the previous process, it may be determined that a stop condition is satisfied and iteration may stop. Or, when the number of repetitions of the process reaches a preset number, it may be determined that the stop condition is satisfied and the repetition may be ended.

Figure 7:
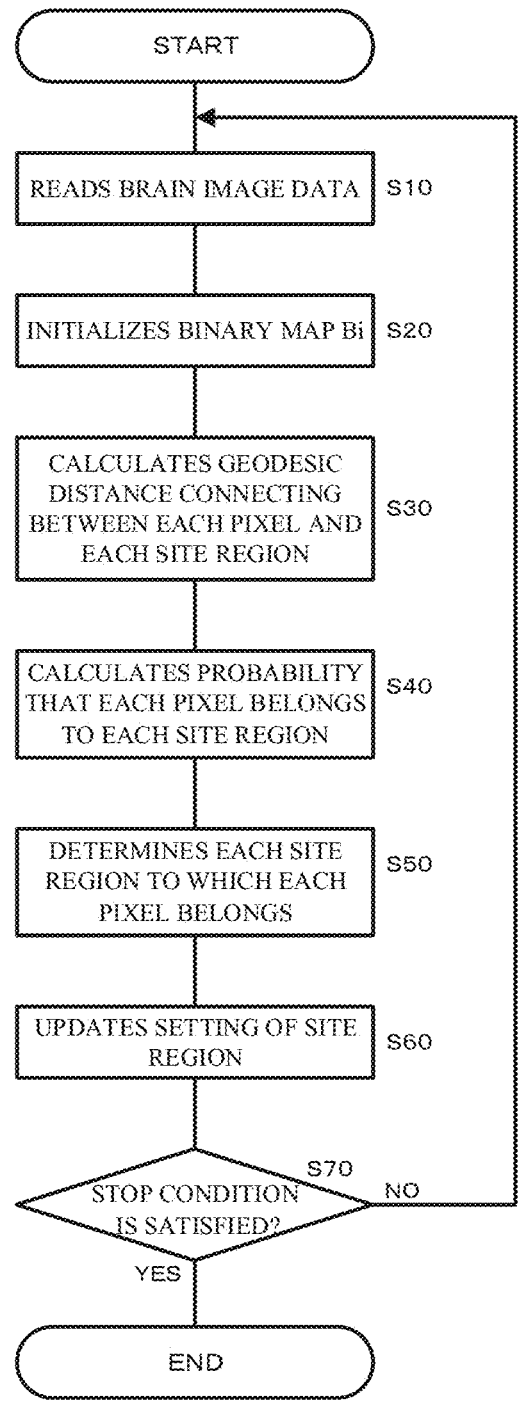
FIG. 7 is a flowchart showing a process flow performed by the brain image data processing apparatus 100.

FIG. 7 is a flowchart showing a process flow performed by the brain image data processing apparatus 100 according to the present embodiment. The process shown in FIG. 7 is performed by the control device 101 as the program that is activated when execution of the program is instructed by the operator of the brain image data processing apparatus 100.

In Step S10, the control device 101 reads the brain image data in which the site region is set from the recording device 102. Thereafter, the process proceeds to Step S20.

In Step S20, as described above, the control device 101 initializes the binary map $B_i$ using Equation (1). Thereafter, the process proceeds to Step S30.

In Step S30, as described above, the control device 101 uses Equation (2) to calculate the distance D(x, B, I) of the geodesic line connecting between each pixel x and each site region $I_i$ for each pixel not included in any site region. Thereafter, the process proceeds to Step S40.

In Step S40, as described above, the control device 101 calculates the probability $p(x|I_i)$ that each pixel x belongs to each site region $I_i$ using Expression (5). Thereafter, the process proceeds to Step S50.

In Step S50, as described above, the control device 101 determines which site region the pixel x belongs to using Equation (6). Thereafter, the process proceeds to Step S60.

In Step S60, as described above, the control device 101 updates the setting of the site region so that the pixel newly determined to belong to the site region belongs to each site region in the brain image data based on the result of Equation (6), to obtain the new brain image data. Thereafter, the process proceeds to Step S70.

In Step S70, as described above, the control device 101 determines whether the stop condition of the process from Step S10 to Step S60 is satisfied. If a negative determination is made in Step S70, the process returns to Step S10, the brain image data after updating the setting of the site region is newly read, and the process from Step S10 to Step S60 is repeated. On the other hand, when a positive determination is made in Step S70, the process ends.

According to the present embodiment described above, the following operational effects can be obtained.

(1) The control device 101 reads the brain image data in which the site region for identifying each region is set at a position corresponding to each site of the brain, calculates the probability that each pixel is included in each site region based on the geodesic distance between each pixel and each site region for each pixel not included in any site region in the read brain image data, and determines which site region each pixel belongs to, based on the calculated probability. Thus, even if accuracy of the site region set in the brain image is low, and the pixel that should originally be included in the site region is located outside the site region, it is possible to determine that the pixel belongs to the site region to which it should originally belong. Further, if a linear distance between each pixel and each site region is used as the distance for calculating the probability, there is a possibility that features such as changes in edges and luminance in an entire image are ignored, and calculation accuracy of the probability decreases. However, by using the geodesic distance between each pixel and each site region, such a problem can be solved and the probability can be calculated in consideration of the features of the image.

(2) The control device 101 updates the setting of the site region in the brain image data so as to include the pixels determined to belong to each part region. Thus, it is possible to improve the setting accuracy of the site region in the brain image data. Further, if the setting accuracy of the site region can be improved, by comparing the image of a patient's brain taken in the past and the latest image of the patient's brain, it is possible to detect diseases such as Alzheimer's affected by a change in volume (cross-sectional area) of a specific site of the brain with high accuracy.

(3) When the calculated probability is larger than a preset threshold value, the control device 101 determines that a target pixel belongs to the site region. Thus, when the probability is less than the threshold value, since the pixel is not determined to belong to the site region, accuracy of determining whether each pixel belongs to any site region can be improved.

(4) The control device 101 repeats a series of processes until a preset stop condition is satisfied, for the brain image data after updating the setting of the site region. This can further improve the setting accuracy of the site region.

(5) When the setting of the site region in the brain image data is not changed from the previous process, or when the number of repetitions of the process reaches the preset number, the control device 101 determines that the stop condition of the process is satisfied. Thus, the process can end at a stage when improvement of the setting accuracy of the site region is expected.

—Modification—

The brain image data processing apparatus 100 according to the above-described embodiment can also be modified as follows.

(1) In the above-described embodiment, as shown in FIGS. 2 to 6, an example in which the process is performed on two-dimensional brain image data has been described. However, the above process may be performed on three-dimensional brain image data created by superimposing a cross-sectional brain image of the subject captured by MRI, CT or the like. For example, voxel data is used as the three-dimensional brain image data. In this case, the process performed on each pixel x of the image data in the above process only has to be performed on three-dimensional pixels, that is, voxels in a three-dimensional image space.

The present invention is not limited to the configuration in the above-described embodiment as long as the characteristic functions of the present invention are not impaired. Further, the above-described embodiment and a plurality of modifications may be combined.

The disclosure content of the following priority basic application is incorporated herein by reference.

Japanese Patent Application No. 2017-104337 (filed on May 26, 2017)

LIST OF REFERENCE NUMERALS

100: Brain image data processing apparatus
101: Control device
102: Recording device

The invention claimed is:

1. A brain image data processing apparatus comprising a processor configured to perform:
a brain image data reading for reading image data taken by MRI (magnetic resonance imaging) or CT (computer tomography), in which site regions for identifying each site are set at positions corresponding to each site of a brain;
probability calculation for calculating a probability that each pixel is included in each site region based on a distance between each pixel and each site region for each pixel not included in any site region in the brain image data read by the brain image data reading; and
a determination for determining which site region each pixel belongs to, based on the probability calculated by the probability calculation,
wherein in the probability calculation, a geodesic distance between each pixel and each site region is calculated for each pixel not included in any site region, and the probability that each pixel is included in each site region is calculated based on the geodesic distance, and
wherein the processor is further configured to perform an updating for updating setting of the site region in the brain image data so as to include the pixels determined to belong to each site region based on a determination result by the determination.

2. The brain image data processing apparatus according to claim 1, wherein in the determination, it is determined that a target pixel belongs to the site region when the probability calculated by the probability calculation is larger than a preset threshold value.

3. The brain image data processing apparatus according to claim 1, wherein the processor is further configured to perform process repeating for repeating a process by the probability calculation, the determination, and the updating until a preset stop condition is satisfied, for the brain image data in which the setting of the site region has been updated by the updating.

4. The brain image data processing apparatus according to claim 3, wherein in the process repeating, it is determined that the stop condition is satisfied when the setting of the site region in the brain image data is not changed from a previous process.

5. The brain image data processing apparatus according to claim 3, wherein in the process repeating, it is determined that the stop condition is satisfied when the number of repetitions of the process reaches a preset number.

6. A brain image data processing method for causing a computer to perform the following steps:
a brain image data reading step of reading brain image data, taken by MRI (magnetic resonance imaging) or CT (computer tomography), in which site regions for identifying each site are set at positions corresponding to each site of a brain;
a probability calculation step of calculating a probability that each pixel is included in each site region based on a distance between each pixel and each site region for each pixel not included in any site region in the brain image data read in the brain image data reading step; and
a determination step of determining which site region each pixel belongs to, based on the probability calculated by the probability calculation step,
wherein the probability calculation step calculates a geodesic distance between each pixel and each site region for each pixel not included in any site region, and calculates the probability that each pixel is included in each site region based on the geodesic distance, and
wherein the method further comprises an updating step for updating setting of the site region in the brain image data so as to include the pixels determined to belong to each site region based on a determination result by the determination step.

7. The brain image data processing method according to claim 2, wherein the determination step determines that a target pixel belongs to the site region when the probability calculated by the probability calculation step is larger than a preset threshold value.

8. The brain image data processing method according to claim 6, further comprising a process repeating step of repeating a process by the probability calculation step, the determination step, and the updating step until a preset stop condition is satisfied, for the brain image data in which the setting of the site region has been updated by the updating step.

9. The brain image data processing method according to claim 8, wherein the process repeating step determines that the stop condition is satisfied when the setting of the site region in the brain image data is not changed from a previous process.

10. The brain image data processing method according to claim 8, wherein the process repeating step determines that the stop condition is satisfied when the number of repetitions of the process reaches a preset number.

11. A non-transitory computer-readable medium storing a brain image data processing program for causing a computer to perform the following steps:
a brain image data reading step of reading brain image data taken by MRI (magnetic resonance imaging) or CT (computer tomography), in which site regions for identifying each site are set at positions corresponding to each site of a brain;
a probability calculation step of calculating a probability that each pixel is included in each site region based on a distance between each pixel and each site region for each pixel not included in any site region in the brain image data read in the brain image data reading step; and
a determination step of determining which site region each pixel belongs to, based on the probability calculated by the probability calculation step,
wherein the probability calculation step calculates a geodesic distance between each pixel and each site region for each pixel not included in any site region, and calculates the probability that each pixel is included in each site region based on the geodesic distance, and
wherein the steps further comprises an updating step for updating the setting of the site region in the brain image data so as to include the pixels determined to belong to each site region based on a determination result by the determination step.

12. The non-transitory computer-readable medium storing the brain image data processing program according to claim 11, wherein the determination step determines that a target pixel belongs to the site region when the probability calculated by the probability calculation step is larger than a preset threshold value.

13. The non-transitory computer-readable medium storing the brain image data processing program according to claim 11, further comprising a process repeating step of repeating a process by the probability calculation step, the determination step, and the updating step until a preset stop condition is satisfied, for the brain image data in which the setting of the site region has been updated by the updating step.

14. The non-transitory computer-readable medium storing the brain image data processing program according to claim 13, wherein the process repeating step determines that the stop condition is satisfied when the setting of the site region in the brain image data is not changed from a previous process.

15. The non-transitory computer-readable medium storing the brain image data processing program according to claim 13, wherein
the process repeating step determines that the stop condition is satisfied when the number of repetitions of the process reaches a preset number.

* * * * *